US006931270B2

(12) United States Patent
Daft et al.

(10) Patent No.: US 6,931,270 B2
(45) Date of Patent: Aug. 16, 2005

(54) METHOD AND SYSTEM FOR CONDUCTING MEDICAL IMAGING TRANSACTIONS

(75) Inventors: Christopher Mark William Daft, Pleasanton, CA (US); William Macomber Leue, Albany, NY (US)

(73) Assignee: General Electric Company, Niskayuna, NY (US)

(*) Notice: Subject to any disclaimer, the term of this patent is extended or adjusted under 35 U.S.C. 154(b) by 600 days.

(21) Appl. No.: 10/072,254

(22) Filed: Feb. 11, 2002

(65) Prior Publication Data

US 2003/0153816 A1 Aug. 14, 2003

(51) Int. Cl.[7] .............................. A61B 5/00; G06F 17/00
(52) U.S. Cl. ............................ 600/407; 705/3; 715/700
(58) Field of Search ................................ 600/410, 425, 600/443, 407, 437, 459; 709/217–219; 715/700; 707/1, 10; 705/2, 3

(56) References Cited

U.S. PATENT DOCUMENTS

| | | | |
|---|---|---|---|
| 5,452,416 A | * 9/1995 | Hilton et al. ............... | 715/783 |
| 5,715,823 A | 2/1998 | Wood et al. | |
| 5,857,967 A | 1/1999 | Frid et al. | |
| 5,891,035 A | 4/1999 | Wood et al. | |
| 6,245,016 B1 | * 6/2001 | Daft et al. ................... | 600/443 |
| 6,529,876 B1 | * 3/2003 | Dart et al. ...................... | 705/4 |
| 6,760,755 B1 | * 7/2004 | Brackett ...................... | 709/214 |
| 2003/0028113 A1 | * 2/2003 | Gilbert et al. .............. | 600/447 |
| 2003/0154062 A1 | * 8/2003 | Daft et al. ...................... | 703/5 |
| 2004/0153862 A1 | * 8/2004 | Grellmann et al. ............ | 714/43 |

OTHER PUBLICATIONS

Software to Track Customers' Needs Helped Firms React by Chris Gaither dated Oct. 1, 2001 Technology The New York Times http://www.nytimes.com/2001/10/01/technology/ebusiness/01CRM.html?todaysheadlines=.

* cited by examiner

Primary Examiner—Shawna J. Shaw
(74) Attorney, Agent, or Firm—Jean K. Testa; Christian G. Cabou

(57) ABSTRACT

Method and system for remotely conducting medical imaging transactions conducive to meeting the individualized imaging needs of a plurality of users are provided. The method provides a user interface configured to present a menu of prompts to a user of a respective medical imager and/or imaging equipment associated with the imager. The menu of prompts is configured to elicit information indicative of imaging performance of the medical imager and/or equipment relative to imaging preferences of the user. The method further allows transmitting the information indicative of the imaging performance over a communications network to an imaging service center. A database is configured to store the information indicative of the imaging performance of the medical imager and/or imaging equipment. The database is further configured to store the imaging preferences of the user. The information stored in the database is processed relative to a set of business rules to select imaging upgrades configured to improve the operational performance of the medical imager. The imaging upgrades are transmitted to reconfigure the imager and/or associated equipment so that the individualized imaging needs of each user are achieved based on the imaging upgrades.

12 Claims, 2 Drawing Sheets

METHOD AND SYSTEM FOR CONDUCTING MEDICAL IMAGING TRANSACTIONS

The present invention is generally related to E-commerce transactions, and, more particularly, to method and system for remotely conducting medical imaging transactions conducive to meeting the individualized imaging needs of a plurality of users.

A. The assignee of the present invention, through its GE Medical Systems business component, is a global supplier of medical imaging systems, such as ultrasound imaging, magnetic resonance imaging, X-ray imaging, computed tomography, nuclear imaging, etc. It will be appreciated that meeting the needs of a worldwide customer base presents substantial challenges, since:

1. Large numbers of the customers are situated in remote parts of the world with relatively low service delivery.

2. It may be cost-prohibitive to allocate the manpower that would be needed to adequately capture, using traditional techniques, the opinions of the majority of the customers. For example, one has traditionally relied on the views of a few US-based "luminary" sites whose views unfortunately may not necessarily correlate strongly with those of the average customer, from whom the bulk of revenues are derived.

3. Customer requirements may vary dramatically from one country to another. Efforts so far to appropriately allocate engineering resources to match this global diversity have been only successful in part. Thus, it would be desirable to become a supplier that more accurately and systematically reflects the views of its global customer base, as opposed to being somewhat limited to any specific region.

B. The assignee of the present invention commonly receives a great deal of feedback information from salespeople and field service engineers. However, under present information-gathering techniques, most of this information is not necessarily relevant or useful. For example, users, such as physicians, clinicians, medical technicians, medical researchers, etc., have no meaningful way of understanding the tradeoffs involved in the design of a given imager. This creates a "language barrier" frustrating any attempts to translate customer needs into product features. Example: a common field service comment may be "Europe dislikes the TV/TR probe of a given ultrasound imaging system." Although the designer team of the supplier may be generally aware of such type of comments, such designer team may lack sufficiently specific information to solve the individualized needs of every customer, since they cannot visit every customer located at far-flung sites who complains, and communicating via the sales organization may be too indirect.

C. Customers are commonly unable to change the imager's behavior beyond a few factory-determined settings. Much of a modem imager is under software control, but at this time much specialized knowledge is required to optimize most of the features for a given clinical application. Present techniques are not conducive to letting the customer make these optimizations. For example, the system designers presently have no means of capturing the way the customer uses the imager on a day-to-to basis, which would be one key information for further image optimization. It is expected that in the future, more and more of the imager features will be implemented via software. If the "language barrier" were removed, after-market upgrades of imaging processing algorithms and/or imaging control parameters would be possible on a per-customer basis.

D. Physicians often have trouble determining if the image quality of the imaging system has degraded. This may result in a relatively large number of unnecessary field service calls, since the customer has no objective way of verifying how the image should look in a particular application.

Method and system for remotely conducting medical imaging transactions conducive to meeting the individualized imaging needs of a plurality of users are provided. The method provides a user interface configured to present a menu of prompts to a user of a respective medical imager and/or imaging equipment associated with the imager. The menu of prompts is configured to elicit information indicative of imaging performance of the medical imager and/or equipment relative to imaging preferences of the user. The method further allows transmitting the information indicative of the imaging performance over a communications network to an imaging service center. A database is configured to store the information indicative of the imaging performance of the medical imager and/or imaging equipment. The database is further configured to store the imaging preferences of the user. The information stored in the database is processed relative to a set of business rules to select imaging upgrades configured to improve the operational performance of the medical imager. The imaging upgrades are transmitted to reconfigure the imager and/or associated equipment so that the individualized imaging needs of each user are achieved based on the imaging upgrades In view of the foregoing discussion, it would be desirable to provide computer-based techniques and tools that facilitate E-commerce transactions via an imaging service center, such as may be managed and operated by the assignee of the present invention, that enable the customer to optimize the performance of imaging systems already deployed at their facilities. Examples of such transactions may include the sale of aftermarket software, such as files comprising optimized operational parameter for a given clinical application or processing algorithms similarly optimized. The transactions may further include purveying new imaging probes to an installed base of ultrasonic imagers, for example. It would be further desirable to better target new product introductions to satisfy the majority of existing and/or prospective customers through improved communication using, for example, an internet-based approach to obtaining physician feedback.

It would be further desirable to develop computer-based tools and techniques that quickly and reliably can reassure the physician that their imager is functioning correctly (or dispatching a service call with the appropriate machine diagnostic information, if not.) It would be also desirable to timely inform the customer of additional imaging products and/or services they may need, at the moment when they will be most receptive to that information. Electronic gathering of records of these interactions between the supplier of the medical imaging systems and its customers can effectively guide development of new imaging products and services, and provide an Internet-based channel for the delivery of aftermarket imaging control parameter files and algorithms convenient to the physician and to the supplier of the imaging equipment. Each of these benefits preferably should be achieved in a highly automated fashion that is cost-effective to implement and user-friendly to the customer. This would enable the supplier of the medical imaging systems to become more data-driven in its decision-making, and more responsive from the customer's perspective, regardless of the location of the customer, essentially in a 24×7 business mode of operation.

BRIEF SUMMARY OF THE INVENTION

Generally, the present invention fulfills the foregoing needs by providing in one aspect thereof, a method for remotely conducting medical imaging transactions conducive to meeting the individualized imaging needs of a plurality of users. The method provides a user interface configured to present a menu of prompts to a user of a respective medical imager and/or imaging equipment associated with the imager. The menu of prompts is configured to elicit information indicative of imaging performance of the medical imager and/or equipment relative to imaging preferences of the user. The method further transmits the information indicative of the imaging performance over a communications network to an imaging service center. A database is provided to be accessible to the service center. The database is configured to store the information indicative of the imaging performance of the medical imager and/or imaging equipment. The database is further configured to store the imaging preferences of the user. The information stored in the database is processed relative to a set of business rules to select imaging upgrades configured to improve the operational performance of the medical imager. The imaging upgrades are transmitted to reconfigure the imager and/or associated equipment so that the individualized imaging needs of each user are achieved based on the imaging upgrades.

The present invention further fulfills the foregoing needs by providing in another aspect thereof, a system for remotely conducting medical imaging transactions conducive to meeting the individualized imaging needs of a plurality of users. The system includes a user interface configured to present a menu of prompts to a user of a respective medical imager and/or imaging equipment associated with the imager. The menu of prompts is configured to elicit information indicative of imaging performance of the medical imager and/or equipment relative to imaging preferences of the user. A communications device is configured to transmit the information indicative of the imaging performance over a communications network to an imaging service center. A database is accessible to the service center. The database is configured to store the information indicative of the imaging performance of the medical imager and/or imaging equipment. The database is further configured to store the imaging preferences of the user. A processor is configured to process the information stored in the database relative to a set of business rules to select imaging upgrades configured to improve the operational performance of the medical imager. A communications device is configured to transmit the imaging upgrades to reconfigure the imager and/or associated equipment so that the individualized imaging needs of each user are achieved based on the imaging upgrades.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

Figure 1:
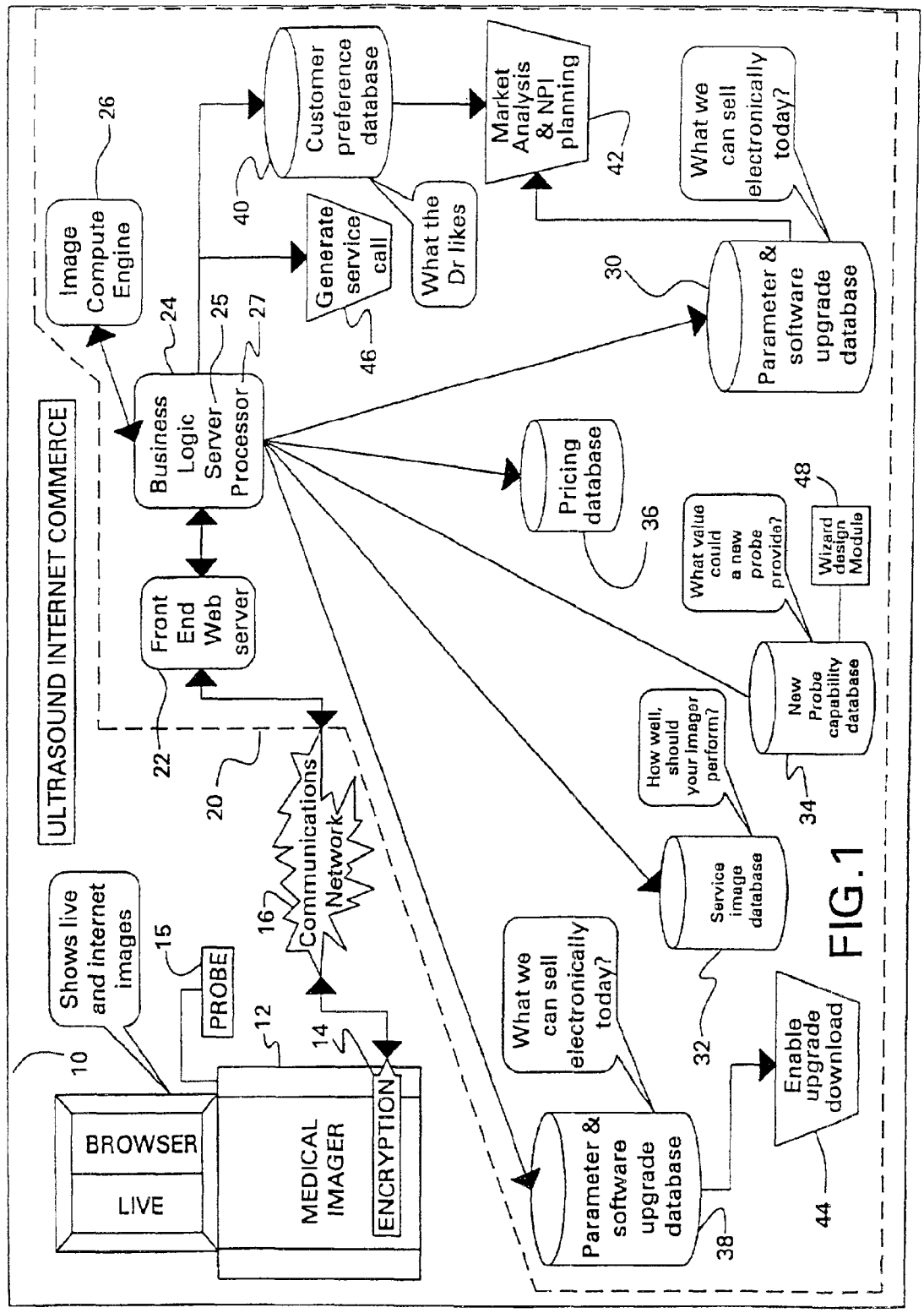
FIG. 1 is a block diagram representation of exemplary building components of a computer-based system in accordance with aspects of the present invention.

FIG. 1 illustrates a block diagram representation of exemplary building components of a computer-based system 10 in accordance with aspects of the present invention. In one exemplary embodiment, the system could begin operation when either:

The user of a particular imager 12 and/or imaging equipment associated with the imager, such as an imaging probe or scanner 15, is dissatisfied with the image quality they have just obtained. In this case, Internet-based processing may be used as further described below. As used herein, the user may comprise any of a variety of individuals whose profession or trade requires use of medical imaging technology, such as a physician, clinician, medical technician, medical researcher, etc. Throughout this specification any of the above-terms including the term customer are used interchangeably, unless otherwise noted.

The user expresses dissatisfaction to a field service or sales personnel about the image quality of the imager and/or associated equipment. Here, it would be possible for the processing to take place during a service visit on a standard personal computer loaded with the appropriate software, or similar computer equipment such as a laptop or personal digital assistant (PDA) carried by the service or sales personnel.

The system may present an uncomplicated, quick-to-complete, and customer-oriented user interface, such as may be provided via a Web page providing for example a few prompts via a commercially available Web browser 13, such as Microsoft Explorer or equivalent, interconnected to the imaging system. Examples of these prompts or questions may be as follows:

What Would You Like to Improve Most in This Image?

The user from a drop-down menu included in the Web page could select one of several possible answers. In addition, a field for entering supplemental comments could be used for entering information that may help the user to better amplify or clarify issues of concern regarding a specific imaging situation. Possible answers in the drop-down menu, assuming an exemplary ultrasound imaging system, may be as follows:

Axial Resolution
Slice Thickness
Lateral Resolution
Frame Rate
Cyst clearing
Sensitivity Which Mode Are You Most Concerned About?

Possible answers selected from a drop-down menu associated with the above-listed question may be as follows:

B-mode
Color Flow
Power Doppler
Pulse Doppler
CW Doppler
Harmonic Imaging
Coded Excitation Which Part of the Image is Most in Need of Improvement?

Here, it is contemplated that the user using a standard computer interface device, such as a computer mouse, or pointer, would draw or highlight on the image to indicate if the problem is off-axis, near-field, etc.

Would You Like to Check the Performance of Your Imager to See if There is a Fault? (Yes/No)

If this answer is Yes, the user is given the opportunity to scan a phantom image. That image would then be uploaded to an e-commerce imaging service center 20, such as may be managed and operated by the assignee of the present invention, and compared with the expected performance of the probe and imager.

After answering these questions, the user clicks a SEND button on the browser. The responses may be encrypted using a commercially available encryption module 14 and sent via a suitable communications network 16 to the e-commerce service center. Although the ubiquitous Internet presently comprises one cost-effective communications network, it will be appreciated that the present invention is not limited to the Internet. For example, wide or local area communications networks, intranets, cellular or wireless communications networks, satellite-based networks, etc., could be used in lieu of or in combination with the Internet. In one exemplary embodiment, the service center 20 is arranged as a three-tier architecture with a front-end web server 22, a server 24, and back-end capabilities, such as an image compute engine 26 and a database that for purposes of explanation may be segmented into a plurality of databases 30, 32 . . . and 40, as described in greater detail below. In one exemplary embodiment server 24 may comprise two or more host computers, conceptually represented by blocks 25 and 27 in FIG. 1, one of which (e.g., block 25) would function as a "server", that is, this host computer would mainly deal with networking protocols and moving data to and from client systems, such as imager 12. One or more other host computers represented by block 27 in FIG. 1 would function as "processors", that is, these other host computers would be used for transforming data and performing computations. A three-tier architecture is believed to provide a cost-effective division of the functional inter-relationships for performing the appropriate input/output of data, as well as data processing and storage. It will be appreciated, however, that the techniques of the present invention are not limited to any specific architecture.

In one exemplary embodiment, the front-end web server 22 may be configured to receive imaging parameters and user-imaging preferences from the remote imager, e.g., imager 12, using Hypertext Transfer Protocol (HTTP). It will be appreciated that as further advances occur in Internet-based technology other protocols not yet presently available could be used in lieu of HTTP. This embodiment allows transmitting back web pages showing the improvements possible with the proposed enhancements. As suggested above, the server 24 processes business rules indicative of an appropriate interaction with any given customer using data from one or more of the plurality of the databases, such as a database 30 configured to store data indicative of production probes imaging capability, a database 32 configured to store service reference images, a database 34 configured to store imaging capabilities that may be achieved with a new probe design, a database 36 configured to store pricing for services and/or products provided by the supplier of the imaging equipment, a database 38 configured to store imaging upgrades, such as upgraded imaging processing algorithms and/or imaging parameters, and a database 40 configured to store user imaging preferences. For example, database 40 may be used for accumulating historical information indicative of the imaging performance of the medical imager and/or associated imaging equipment relative to imaging preferences of each user for a plurality of corresponding imagers and/or equipment. That is, a fleet of imagers and/or associated imaging equipment deployed in the field and belonging to a commons class of imaging systems.

In one exemplary embodiment, server 24 logs every customer/supplier interaction to the customer preference database 40, which may be regularly analyzed by appropriate personnel of the supplier to guide New Product Introduction (NPI) resource allocations using, for example, an NPI processing module 42 based on trends and/or patterns of imaging preferences of users. The business logic processor also submits requests to the Image Compute Engine 26 to selectively activate imaging parameters and algorithm selections that would be conducive for creating more realistic images for a given probe and/or clinical application.

The operation of the e-commerce imaging service center in one exemplary embodiment is contemplated to be as follows:

1) The machine ID, probe and parameter settings may be recorded in the customer preference database, along with the physician's image quality concern. These data are accumulated and processed with responses from other customers and used to target future NPIs in a data-driven fashion.

2) An appropriate computer phantom for image quality comparisons may be selected, based, for example, on the specific imager's probe, selected imaging parameters, mode and area of concern to the user.

3) The imaging parameters and system software databases may be searched to identify candidate imaging data files or algorithms appropriate to the imaging needs of each respective user. Imaging parameters and processing algorithms may be configured to improve the image in essentially the exact way any given customer desires—for example, the far-field signal-to-noise ratio may be important to a given customer, but frame rate may be less important to that customer. The reverse could be true for another customer. As suggested above, a set of imaging parameters appropriate to a given probe and/or clinical application can be downloaded to configure the imager to emphasize a different imaging objective than the one it could be achieved using the factory-set imaging parameters the equipment is shipped with. If a number of customers express a need for similar changes via the e-commerce system, then the supplier of the imaging equipment would be able to consider altering its standard system software to accommodate the collective needs of the customers. In this way, the engineering organization of the supplier may be responsive to statistically reliable preference data collected from each customer.

4) The available production probes database 30 may be searched to identify any alternative probes, which would solve a given imaging issue. This may provide a business opportunity for the supplier to showcase any appropriate technology available to that supplier, e.g., GE's Active Matrix Array imaging technology, at a point of relatively high customer interest.

5) Imaging simulations may be performed using a computer-generated phantom or reference image and:

Present imager, probe, algorithms and imaging parameters;

Candidate imaging parameter enhancements;

Candidate processing algorithm enhancements; or

Candidate probe alternatives

6) A pricing lookup may be performed for each imaging configuration alternative, and one or more web pages may be transmitted via the communications network to the remote imager's browser. For each of these options, the user may be presented with "before" and "after" images that respectively illustrate the benefits of each solution proposed. This causes the interaction about imaging preferences to occur in the user's preferred domain, i.e., essentially via medical images based on the individualized imaging preferences of the user. The doctor can immediately see imaging options that allow improving the final product, and maintaining affordable costs. Some of these imaging options (erg., optimized imaging parameters and processing algorithms) will be immediately available for electronic download. The imager would include a download software module 44 to automatically install such purchased enhancements, somewhat analogous to "auto-update" technology in PC applications, such as RealPlayer.

The doctor can respond using web forms or pages in one of several exemplary ways:

I'd like to buy an imaging parameter set. A credit card, or institutional billing code would allow immediate download from the e-commerce data center of the appropriate imaging parameter set for a given application.

I'd like to buy an advanced algorithm. Essentially same instant delivery mechanism as outlined above.

I'd like to order the probe you recommended. Upon receipt of billing information (handled securely via the web browser) a probe suitable to meet the needs of the customer would be dispatched from the factory.

Your phantom or reference image did not adequately represent my clinical issue. In this case the doctor would be invited to highlight the appropriate anatomical features on the live (but static) image presented on the screen of the imaging equipment. The remote Web server would be configured to upload these imaging data, and, for example, estimate scattering strengths and perform basic image analysis (feature extraction). It can then make a new phantom image, which is recorded in the customer preference database. A new image simulation would then be performed using the new phantom image, and new imaging options based on the new phantom image would be sent back to the doctor.

Based on these images, I think my system is faulty. Your images are much better than what I see on the live display. This type of issue can be verified using the approach described in the previous paragraph. If the physician still is of this opinion, a service call would be automatically initiated via a service call module 46, and comprehensive diagnostics and troubleshooting procedures may be initiated using the InSite diagnostic services provided by the assignee of the present invention.

None of the upgrade options you showed me are good enough. A Web page may be configured to ask the doctor if they would like to design a new probe. For example, a probe design wizard 48 would be started as an applet in the physician's browser. Using the new probe design database 34, the physician would be guided or assisted by the wizard 48 through the probe design in a practical and economically manufacturable way, and show the probable image quality that could be achieved with the new probe and including a cost estimate. The new probe design configured to achieve any desired imaging preferences of a given customer would be recorded in the customer preference database 40.

Figure 2:
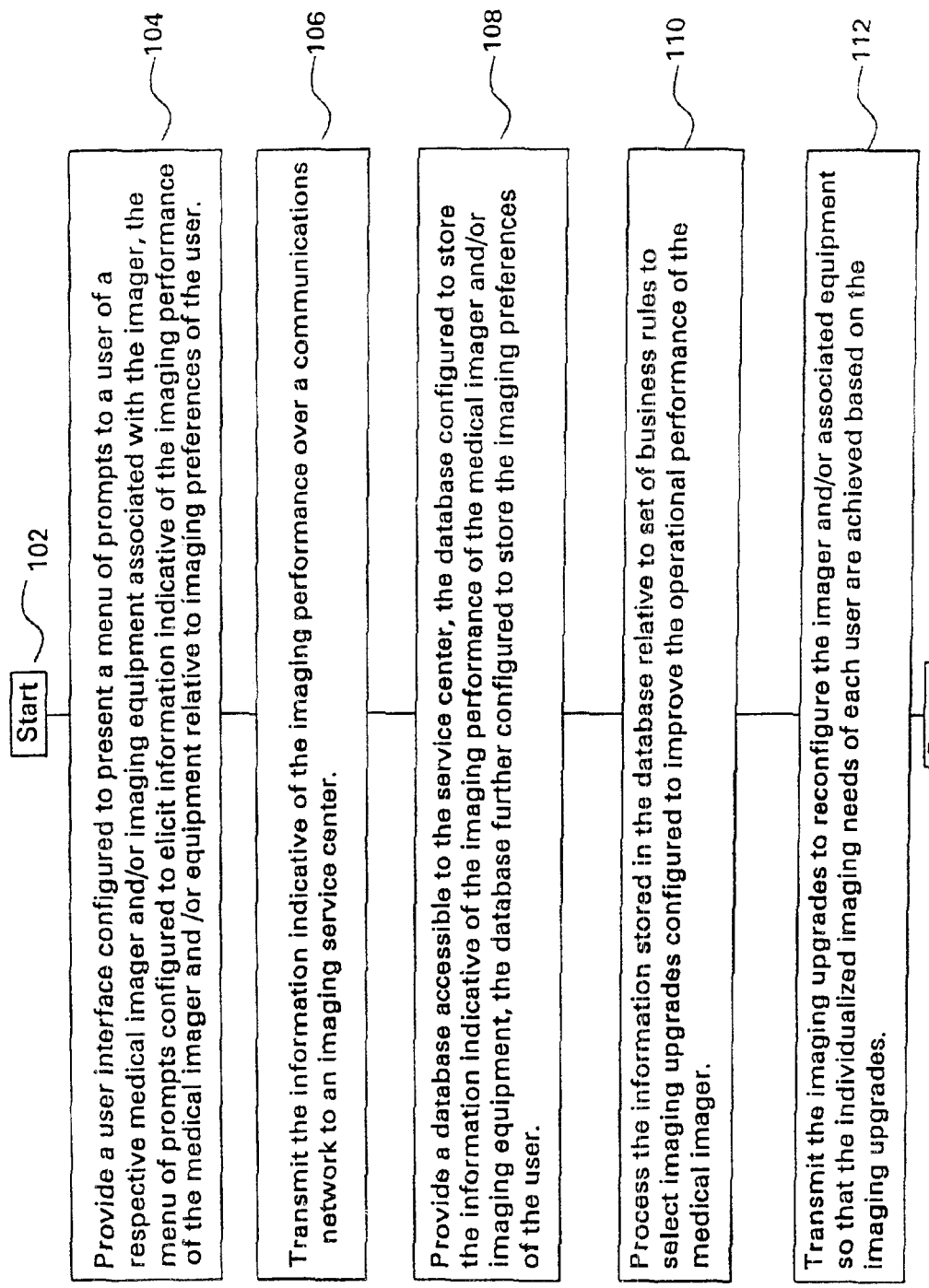
FIG. 2 is a flow chart depicting exemplary steps or actions that may be implemented with the system of FIG. 1 for performing a method for remotely conducting medical imaging transactions conducive to meeting the individualized imaging needs of a plurality of users.

FIG. 2 illustrates a flow chart 100 depicting exemplary steps or actions for implementing a method for remotely conducting medical imaging transactions conducive to meeting the individualized imaging needs of a plurality of users. Subsequent to a starting step 102, at block 104, the method provides a user interface (e.g., Web browser 13 (FIG. 1) configured to present a menu of prompts to a user of a respective medical imager 12 and/or imaging equipment associated with the imager, e.g., imaging probe 15. The menu of prompts is configured to elicit information indicative of imaging performance of the medical imager and/or equipment relative to imaging preferences of the user. The method further allows at block 106 to transmit the information indicative of the imaging performance over a communications network 16 to an imaging service center 20. As illustrated at block 108, a database, such as may be made-up of a collection of databases (e.g., databases 30, 32 . . . and 40 (FIG. 1)), is provided to be accessible to the service center. The database is configured to store the information indicative of the imaging performance of the medical imager and/or imaging equipment. The database is further configured to store the imaging preferences of the user. As illustrated at block 110, the information stored in the database is processed relative to a set of business rules to select imaging upgrades configured to improve the operational performance of the medical imager. Prior to return step 114, at block 112, the imaging upgrades are transmitted to reconfigure the imager and/or associated equipment so that the individualized imaging needs of each user are achieved based on the imaging upgrades. The imaging upgrades may comprise an upgraded set of imaging parameters for controlling the imager and/or upgraded imaging processing algorithms. The imaging upgrade may further comprise selecting a probe from a database of available production probes for the imager or selecting a new probe design configured to meet a desired imaging preference of the user. In one exemplary embodiment, the new probe design may be based on design assistance derived from a probe design wizard accessible by the user through the communications network. The database may be used for accumulating historical information indicative of the imaging performance of the medical imager and/or equipment relative to imaging preferences of each user for a plurality of corresponding imagers and/or equipment. For example, the accumulated historical information may be processed to determine trends regarding user-imaging preferences. The imaging trends in turn may be used for determining allocation of economic resources of the supplier for developing new imaging products and/or services. In one exemplary embodiment, the information indicative of the imaging performance transmitted to the imaging service center may include an image, e.g., a phantom image, generated subject to the imaging preferences of the user. The phantom image may then be compared relative to reference images corresponding to the imaging preferences of the user, and, based on the results of the comparison, a recommendation may be issued to the user regarding the condition of the medical imager and/or imaging equipment. This would advantageously avoid or substantially reduce unnecessary and costly service calls.

The present invention can be embodied in the form of computer-implemented processes and apparatus for practicing those processes. The present invention can also be embodied in the form of computer program code containing computer-readable instructions embodied in tangible media, such as floppy diskettes, CD-ROMs, hard drives, or any other computer-readable storage mediums wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose computer, the computer program code segments configure the computer to create specific logic circuits or processing modules.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method for remotely conducting medical imaging transactions conducive to meeting the individualized imaging needs of a plurality of users, the method comprising:
   providing a user interface configured to present a menu of prompts to a user of a respective medical imager and/or imaging equipment associated with the imager, the menu of prompts configured to elicit information indicative of imaging performance of the medical images and/or equipment relative to imaging preferences of the user;
   transmitting the information indicative of the imaging performance over a communications network to an imaging service center;
   providing a database accessible to the service center, the database configured to store the information indicative of the imaging performance of the medical imager and/or imaging equipment wherein the information indicative of the imaging performance transmitted to the imaging service center comprises an image generated subject to the imaging preferences of the user, the database further configured to store the imaging preferences of the user;
   processing the information stored in the database relative to a set of business rules to select imaging upgrades configured to improve the operational performance of the medical imager;
   transmitting the imaging upgrades to reconfigure the imager and/or associated equipment so that the individualized imaging needs of each user are achieved based on the imaging upgrades; and,
   comparing the transmitted image relative to reference images corresponding to the imaging preferences of the user, and, based on the results of the comparison, issuing a recommendation to the user regarding the medical imager and/or imagine equipment.

2. The method of claim 1 wherein the imaging upgrades comprise an upgraded set of imaging parameters for controlling the imager and/or upgraded imaging processing algorithms.

3. The method of claim 1 wherein the imaging equipment comprises an imaging probe and the imaging upgrade comprises selecting a probe from a database of available probes for the imager.

4. The method at claim 1 wherein the imaging equipment comprises an imaging probe and the imaging upgrade comprises selecting a new probe design configured to meet a desired imaging preference of the user.

5. The method of claim 1 wherein the medical imager is selected from the group consisting of ultrasound, magnetic resonance, X-ray, computer tomography, and nuclear imagers.

6. The method of claim 1 further comprising accumulatin, historical information indicative of the imaging performance of the medical imager and/or equipment relative to imaging preferences of each user for a plurality of corresponding imagers and/or equipment.

7. A system for remotely conducting medical imaging transactions conducive to meeting the individualized imaging needs of a plurality of users, the system comprising:
   a user interface configured to present a menu of prompts to a user of a respective medical imager and/or imaging equipment associated with the imager, the menu of prompts configured to elicit information indicative of imaging performance of the medical imager and/or equipment relative to imaging preferences of the user;
   communications device configured to transmit the information indicative of the imaging performance over a communications network to an imaging service center;
   a database accessible to the service center, the database configured to store the information indicative of the imaging performance of the medical imager end/or imaging equipment, the database further configured to store the imaging preferences of the user, wherein the information indicative of the imaging performance comprises an image generated subject to the image preferences of the user;
   a processor configured to process the information stored in the database relative to a set of business rules to select imaging upgrades configured to improve the operational performance of the medical imager, wherein the processor is further configured to compare the image generated subject to the imaging preferences of the user relative to reference images corresponding to the imaging preferences of the user, and, based on the results of the comparison, the processor issues a recommendation to be communicated to the user regarding the medical imager and/or imaging equipment; and
   communications device configured to transmit the imaging upgrades to reconfigure the imager and/or associated equipment so that the individualized imaging needs of each user are achieved based on the imaging upgrades.

8. The system of claim 7 wherein the imaging upgrades comprise an upgraded set of imaging parameters for controlling the imager and/or upgraded imaging processing algorithms.

9. The system of claim 7 wherein the imaging equipment comprises an imaging probe and the imaging upgrade comprises selecting a probe from a database of available probes for the imager.

10. The system of claim 7 wherein the imaging equipment comprises an imaging probe and the imaging upgrade comprises selecting a new probe design configured to meet a desired imaging preference of the user.

11. The system of claim 7 wherein the medical imager is selected from the group consisting of ultrasound, magnetic resonance, X-ray, computer tomography, and nuclear imagers.

12. The system of claim 7 further comprising a database configured to accumulate historical information indicative of the imaging performance of the medical imager and/or equipment relative to imaging preference of each user for a plurality of corresponding imagers and/or equipment.

* * * * *